United States Patent [19]

Kato et al.

[11] Patent Number: 5,032,675
[45] Date of Patent: Jul. 16, 1991

[54] PROCESS FOR THE PRODUCTION OF GLUTAMINE DERIVATIVES

[75] Inventors: Toshihisa Kato; Masahiko Kurauchi, both of Kawasaki, Japan

[73] Assignee: Ajinomoto Co., Inc., Tokyo, Japan

[21] Appl. No.: 250,548

[22] Filed: Sep. 29, 1988

[30] Foreign Application Priority Data

Jul. 10, 1987 [JP] Japan .................. 62-253383

[51] Int. Cl.$^5$ .................. C07K 1/00; C07K 1/06
[52] U.S. Cl. .................. 530/337; 530/334; 530/338
[58] Field of Search .................. 530/338, 334, 337

[56] References Cited

U.S. PATENT DOCUMENTS 4,857,555  8/1989  Smith et al. .................. 514/563

OTHER PUBLICATIONS

Bodanszky, M., *Principles of Peptide Synthesis*, Springer-Verlag, pp. 158–159, 160 and 210–211, 1984.
Stewart et al., *Solid Phase Peptide Synthesis*, 2nd Ed., Pierce Chemical Company, 1984, p. 31.
Protection of Amide–Nitrogen for Peptide Synthesis. A Novel Synthesis of *Peptides Containing C-Terminal Glutamine* by Shiro Akabori et al, May 1961, Short Communications, p. 739.
Studies on the Synthesis of Peptides Containing Glutamine as the C-Terminal. I. *Protection of Amide–Nitrogen with Xanthyl Group During Peptide Synthesis* by Yasutsugu Shimonishi et al., vol. 35, No. 12, dated Dec. 1962.
Studies of the Synthesis of Peptides Containing C-Terminal Glutamine. II. *The Synthesis and Use of α-p-Nitrobenzyl γ-Methyl L-Glutamate* by Yasutsugu Shimonishi, vol. 37, No. 2, pp. 200–203, Jan. 1964.
Bull. Chem. Soc. Jap., vol. 35, No. 12, Dec. 1962, pp. 1966–1970; Y. Shimonishi et al.: "Studies on the Synthesis of Peptides Containing Glutamine as the C-Terminal. I. Protection of Amide–Nitrogen with Xanthyl Group During Peptide Synthesis".
Angew. Chem, vol. 71, 1959, pp. 742; J. Rudinger: "Nebenreaktionen bei Peptidesynthesen mit Glutamin und Asparagin".

*Primary Examiner*—Howard E. Schain
*Assistant Examiner*—Susan M. Perkins
*Attorney, Agent, or Firm*—Oblon, Spivak, McClelland, Maier & Neustadt

[57] ABSTRACT

Improved methods for synthesizing glutamine-containing peptides, involving an active ester method between a protected, C-terminal activated amino acid or a protected, C-terminal activated peptide, and unprotected glutamine in the presence of a weak base, are disclosed.

5 Claims, No Drawings

PROCESS FOR THE PRODUCTION OF GLUTAMINE DERIVATIVES

BACKGROUND OF THE INVENTION

1. Field of the Invention

The present invention relates to synthesis of glutamine-containing peptides. More particularly, it relates to a process for the synthesis of glutamine-containing peptides which comprises reacting an N-protected amino acid or peptide with N-hydroxysuccinimide o the like to form an active ester by the use of a condensing agent, such as dicyclohexylcarbodiimide, and subjecting the ester to a reaction with unprotected glutamine in the presence of a weak base, to form a peptide with a C-terminal glutamine, followed by eliminating the N-protective group from the peptide.

2. Description of the Related Art

Glutaimine is an indispensable component of culture media or infusions, but it is very difficult to use glutamine because of its low thermal stability. Glutamine-containing dipeptides exhibit a good thermal stability and can be handled, even at temperature conditions of sterilization.

Glutamine-comtaining dipeptides are highly useful as ingredients for serum-free media. They have also been employed as ingredients for infusions. Their practical importance is thus widespread.

In producing glutamine-containing peptides, it is known that various side reactions are liable to take place due to the instability of the $\beta$-amido group of the glutamine residue, thus making their synthesis quite difficult (see, e.g., J. Rudinger, Angew. Chem., 71, 742 (1959)). Other publications concerning the synthesis of glutamine-containing peptides are listed hereinbelow and are incorporated herein by reference.

(1) Y. Shimonishi, S. Sakakibara and S. Akabori, Bull. Chem. Soc. Jap., 35, 1966–1970.

(2) Y. Shimonishi, Bull. Chem. Soc. Jap., 37, 200–203.

(3) S. Akabori, S. Sakakibara and Y. Shimonishi, Bull. Chem. Soc. Jap., 34, 739.

However, the processes described in the above publications involve significant difficulties if they are to be used as commercial processes. In addition, final products obtained by the processes are contaminated with impurities which are difficult to remove. Furthermore, the processes give only poor yields. For example, when applied to the synthesis of alanylglutamine, the process described in (1) above gives a yield of only ca. 5%, and the process described in (3) above provides a yield of at best ca. 28%. The known processes are therefore by no means satisfactory from a commercial point of view.

There remains a need for improved methods of synthesizing glutamine-containing peptides.

SUMMARY OF THE INVENTION

Accordingly, one object of the present invention is to provide an improved method of synthesizing glutaminyl peptides.

It is also an object of the present invention to enhance the yield and purity of glutaminyl residue-containing peptides.

These and other objects of the present invention as will hereinafter become more readily apparent, have been achieved by the discovery by the present inventors that highly pure glutamine-containing derivatives can be obtained in high yields if produced in accordance with the peptide active ester synthetic approach through formation of a peptide bond between the C-terminal of an amino acid or a peptide and the N-terminal of glutamine, and if the process is carried out in the presence of a weak base, thereby using unprotected glutamine.

DESCRIPTION OF THE PREFERRED EMBODIMENTS

It is preferable to use an N-protected amino acid or peptide. Any of the conventional protective groups may be used, including carbobenzoxy, t-butyloxycarbonyl and benzyl. It is preferable to utilize carbobenzoxy groups because they facilitate crystallization.

As a weak base, there can be used carbonates (e.g., sodium carbonate, potassium carbonate, etc.), hydrogencarbonates (e.g., sodium hydrogencarbonate, potassium hydrogencarbonate, etc.), or the like. Amino acids to be used in the process of the present invention can be D-, L-form, or a racemic mixture. Preferably, the amino acid corresponds to one of the 20 naturally occurring amino acids (with D-, L-, or DL-stereochemistry), and the peptide to which the glutamine is to be attached is a dipeptide, tripeptide, or higher oligopeptide (preferably up to 20 amino acids in length, particularly preferably 2–10) made up of any combination of said D-, L-, or DL-amino acids. The amino acid or peptide to be coupled with glutamine is generally protected on the N-terminal thereof with a protecting group such as Z- or t-Boc-, preferably Z-.

In the case where e.g., Gly-Gln is to be produced according to the process of the present invention, Z-Gly is allowed to react with N-hydroxybenzotriazole or N-hydroxysuccinimide and with a carbodiimide (preferably dicyclohexylcarbodiimide) in a water-miscible solvent, such as dioxane, tetrahydrofuran, acetone, acetonitrile or dimethylformamide (preferably in dioxane or tetrahydrofuran), to form an active ester, and then the ester is allowed to react with unprotected L-glutamine to give Z-Gly-L-Gln. This type of coupling reaction is referred to as the "active ester" method of peptide synthesis, since the reactant which provides the carboxyl side of the peptide bond to be formed is activated by esterification with a group which can be readily displaced by an amino-group containing reactant. The activating group can be any of a number of good leaving groups which are well-known to peptide synthetic chemists. Such groups include, but are not limited to, N-hydroxysuccinimide, pentachlorophenol, chloride, N-hydroxybenzotriazole, para-nitrophenol, and the like. When this group is esterified to an amino acid or peptide, the ester is referred to herein as an active ester intermediate for peptide synthesis. Unprotected glutamine means D, L or DL glutamine which does not contain a chemically blocked amino or carboxyl terminus.

The above reactions are usually carried out at a temperature of from 30° to 20° C. for a period of 1 to 30 hours, preferably from 5 to 10 hours. The thus obtained product, such as Z-Gly-L-Gln is subjected to a treatment for eliminating the protective group by hydrogen, e.g. by hydrogenolysis using a palladiumcarbon catalyst in a mixture of water and an alcohol, preferably methanol or ethanol. This elimination reaction is usually carried out at a temperature of from 10° to 40° C., preferably from 15° to 30° C., for a period of 1 to 3 hours. The elimination of protective groups utilizing hydrogen and palladium-carbon catalyst is almost free from side reactions and therefore is an excellent technique in the production of glutamine-containing peptides.

The progress of the reaction can be followed by thin layer chromatography. After the termination of the reaction has been confirmed, the catalyst is removed by filtration, and then an alcohol (preferably isopropanol or ethanol) is added to the reaction mixture so as to allow the desired product to crystallize in a highly pure state. In the case of alanylglutamine, for example, it can be produced in a yield of 58% when synthesized according to the process of the invention, whereas its yield can be at best 30% in the prior processes. Accordingly, the process of the present invention is advantageous over the prior processes not only in purity but also in yield.

Abbreviations used in this specification are as follows:

Ala: Alanine
Gln: Glutamine
Gly: Glycine
Z: Carbobenzoxy group
t-Boc: t-Butyloxycarbonyl group The invention now being generally described, the same will be better understood by reference to the following examples, which are not intended to limit any aspect of the present invention, unless indicated.

EXAMPLES

Example 1

Synthesis of L-Alanyl-L-Glutamine (a) N-carbobenzoxy-L-alanyl-L-glutamine (Z-L-Ala-L-Gln)

Into a 300 mol round bottom flask were charged 10 g (44.8 mmol) of Z-L-Ala and 5.2 g (45.2 mmol) of N-hydroxysuccinimide, and the contents were dissolved in 100 ml of dioxane. Then, a solution of 9.2 g (44.7 mmol) of dicyclohexylcarbodiimide in 40 ml of dioxane was added dropwise, while the temperature of the reaction mixture wa maintained at 25° to 20° C. After the reaction had been allowed to proceed for 5 hours, precipitated dicyclohexylurea was filtered off. On the other hand, 7.2 g (50 mmol) of L-Gln was dissolved in 70 ml of aqueous 10% sodium hydrogencarbonate solution, and the resulting solution was cooled to 15° to 10° C. The dioxane solution prepared above was then added dropwise to the cooled solution, and the reaction was allowed to proceed for 5 hours. After the completion of the reaction, the pH of the reaction mixture was adjusted to 6.8 with 1N HCl, and the dioxane was distilled off. After insoluble substances were filtered off, its pH was adjusted to 3 to 3.5 with 1N HCl. Crystals precipitated within 1 to 2 minutes, and the crystals were collected by filtration, washed with water and dried under reduced pressure to give 7 g (20 mmol) of Z-L-Ala-L-Gln. The pH of the above mother liquor was adjusted to 2.0 with 1N HCl, so as to precipitate an additional 5 g of Z-L-Ala-L-Gln.

(b) L-alanyl-L-glutamine (L-Ala-L-Gln)

Into a 200 ml three-necked flask was charged 5.0 g (14.2 mmol) of Z-L-Ala-L-Gln, and the peptide was dissolved in 100 ml of a mixture of methanol and water (methanol:water =7:3) and stirred with a magnetic stirrer. After the air in the flask had been replaced with nitrogen, 0.8 g of 2% by weight palladium-carbon was added thereto, and the protective group was eliminated in a stream of hydrogen. After 2 hours, the completion of the reaction was confirmed by thin layer chromatography, and then the palladium-carbon was filtered off. The filtrate was concentrated to 20 ml under reduced pressure, and 40 ml of isopropyl alcohol was added thereto. The resulting mixture was stirred for 30 minutes, during which time crystals precipitated. The crystals were collected by filtration, washed with isopropyl alcohol and then dried under reduced pressure to give 2.8 g (12.9 mmol) (90%) of L-Ala-L-Gln.

m.p.: 205°–207° C. (decomp.)

[α]hd D$^{20}$: +10.5° (C=2.0, H$_2$O)

IR $\gamma_{max}^{KBr}$cm$^{-1}$: 3400, 3350, 1640, 1630, 1600, 1520, 1380, 1150

R$_f$: 0.20 (silica gel, phenol:water=3:1)

EXAMPLE 2

Synthesis of Glycyl-L-Glutamine (a) N-carbobenzoxy-glycyl-L-glutamine (Z-Gly-L-Gln)

Into a 300 ml round bottom flask were charged 10 g (47.8 mmol) of Z-Gly and 5.5 g (47.8 mmol) of N-hydroxysuccinimide, and the contents were dissolved in 100 ml of dioxane. Then, a solution of 9.9 g (48.0 mmol) of dicyclohexylcarbodiimide in 40 ml of dioxane was added thereto, during which time the temperature of the reaction mixture was maintained at 25° to 20° C.

After 4 hours, precipitated dicyclohexylurea was filtered off. On the other hand, 7.2 g (50 mmol) was dissolved in 70 ml of aqueous 10% sodium hydrogencarbonate solution, and the resulting solution was cooled to 15° C. The dioxane solution prepared above was then added dropwise to the cooled solution. After the completion of the reaction, the pH of the reaction mixture was adjusted to 7.0 with 1N HCl, and the dioxane was distilled off. After insoluble substances had been filtered off, the filtrate was adjusted to a pH of 2.0 with 1N HCl and then allowed to stand overnight in a refrigerator. Precipitated crystals were collected by filtration, washed with water and dried under reduced pressure to give 13.2 g (39.2 mmol) (82% based o starting Z-Gly) of Z-Gly-L-Gln.

(b) Glycyl-L-Glutamine (Gly-L-Gln)

Into a 200 ml three-necked flask was charged 10 g (29.7 mmol) of Z-Gly-L-Gln, and 100 ml of 70% aqueous methanol was added thereto with stirring by a stirrer. After the air in the flask had been replaced with nitrogen, 1.5 g of 2% by weight palladium-carbon was added thereto, and the protective group was eliminated in a stream of hydrogen. In the initial stage of the reaction the mixture was in the form of a slurry, but the Z-Gly-L-Gln dissolved as the reaction progressed. After 3 hours, the completion of the reaction was confirmed by thin layer chromatography, and then the palladium-carbon was filtered off. After the filtrate had been concentrated to 30 ml, 40 ml of methanol was added thereto, and the resulting solution was allowed to stand overnight at 5° C., so as to allow crystals to precipitate. The crystals formed were collected by filtration, washed with a small quantity of cold methanol and then dried under reduced pressure to give 4.9 g (22.2 mmol) (75% based on Z-Gly-L-Gln) of Gly-L-Gln.H$_2$O.

m.p.: 198° C. (decomp.)

[α]$_D^{20}$: −1.6° (C=4.0, H$_2$O)

IR$\gamma_{max}^{KBr}$cm$^{-1}$: 3520, 3400, 3250, 3100, 1690, 1570, 1410, 1340, 1280

R$_f$: 0.13 (silica gel, phenol:water 3:1).

The invention now being fully described, it can be seen that additional modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. In a process for producing a peptide containing an L-, D- or DL-glutamine residue through formation of a peptide bond between the C-terminus of an N-protected amino acid or the C-terminus of an N-protected peptide and the N-terminus of glutamine by way of an active ester intermediate for peptide synthesis, the improvement which comprises: forming said peptide bond in the presence of a weak base, by reacting an unprotected L-, D-, or DL-glutamine as a reactant with an active ester of said N-protected amino acid or peptide.

2. A process as defined in claim 1, wherein said amino acid is glycine or alanine.

3. A process as defined in claim 2, wherein said protective group is a carbobenzoxy group.

4. A process as defined in claim 1, wherein said weak base is an alkali metal carbonate or hydrogencarbonate.

5. A process as defined in claim 1, wherein said peptide is one containing from 2 to 10 amino acids, each of which is independently selected from the group consisting of the 20 naturally occurring L-amino acids and their D-and Dl-analogues.

* * * * *